United States Patent
Rosen et al.

(10) Patent No.: US 11,583,392 B2
(45) Date of Patent: Feb. 21, 2023

(54) ACHROMATIC LENSES FOR VISION TREATMENT

(71) Applicant: AMO Groningen B.V., Groningen (NL)

(72) Inventors: Robert Rosen, Groningen (NL); Franck Gounou, Groningen (NL)

(73) Assignee: AMO Groningen B.V., Groningen (NL)

( * ) Notice: Subject to any disclaimer, the term of this patent is extended or adjusted under 35 U.S.C. 154(b) by 8 days.

(21) Appl. No.: 17/103,931

(22) Filed: Nov. 24, 2020

(65) Prior Publication Data

US 2021/0196450 A1    Jul. 1, 2021

Related U.S. Application Data (60) Provisional application No. 62/955,341, filed on Dec. 30, 2019.

(51) Int. Cl.
*A61F 2/16* (2006.01)

(52) U.S. Cl.
CPC .......... *A61F 2/1654* (2013.01); *A61F 2/1637* (2013.01); *A61F 2240/001* (2013.01); *A61F 2240/002* (2013.01); *G02C 2202/20* (2013.01)

(58) Field of Classification Search
CPC ......... A61F 2/16; A61F 2/1613; A61F 2/1654
See application file for complete search history.

(56) References Cited

U.S. PATENT DOCUMENTS

| | | |
|---|---|---|
| 4,655,565 A | 4/1987 | Freeman |
| 5,071,207 A | 12/1991 | Ceglio et al. |
| 5,117,306 A | 5/1992 | Cohen |
| 5,152,787 A | 10/1992 | Hamblen |
| 5,178,636 A | 1/1993 | Silberman |
| 5,201,762 A | 4/1993 | Hauber |
| 5,589,982 A | 12/1996 | Faklis et al. |
| 5,895,422 A | 4/1999 | Hauber |

(Continued)

FOREIGN PATENT DOCUMENTS

| | | |
|---|---|---|
| CN | 104127263 B | 3/2016 |
| EP | 2045648 B1 | 4/2012 |

(Continued)

OTHER PUBLICATIONS

Faklis D., et al., "Spectral Properties of Multiorder Diffractive Lenses", Applied Optics, May 1995, vol. 34 (14), pp. 2462-2468.

(Continued)

*Primary Examiner* — Javier G Blanco
(74) *Attorney, Agent, or Firm* — Johnson & Johnson Surgical Vision, Inc.

(57) ABSTRACT

Apparatuses, systems and methods for providing improved ophthalmic lenses, particularly intraocular lenses (IOLs), include features for reducing dysphotopsia effects, such as haloes and glare. Exemplary ophthalmic lenses can include an optic having a central region disposed about an optical axis and a peripheral region extending outward from the central region, with a diffractive achromat positioned on the peripheral region, and the central region lacking an achromat, and a base power for distance of the central region being the same as a base power for distance of the peripheral region.

18 Claims, 7 Drawing Sheets

(56) References Cited

U.S. PATENT DOCUMENTS

| | | |
|---|---|---|
| 6,266,191 B1 | 7/2001 | Abe |
| 6,366,405 B2 | 4/2002 | Abe |
| 6,536,899 B1 | 3/2003 | Fiala |
| 6,590,708 B2 | 7/2003 | Nakai et al. |
| 6,830,332 B2 | 12/2004 | Piers et al. |
| 6,917,472 B1 | 7/2005 | Yun et al. |
| 6,951,391 B2 | 10/2005 | Morris et al. |
| 7,093,938 B2 | 8/2006 | Morris et al. |
| 7,188,949 B2 | 3/2007 | Bandhauer et al. |
| 7,572,007 B2 | 8/2009 | Simpson |
| 7,677,725 B2 | 3/2010 | Piers et al. |
| 7,717,558 B2 | 5/2010 | Hong et al. |
| 8,231,219 B2 | 7/2012 | Weeber |
| 8,292,952 B2 | 10/2012 | Bille |
| 8,529,623 B2 | 9/2013 | Piers et al. |
| 8,623,083 B2 | 1/2014 | Piers et al. |
| 8,709,079 B2 | 4/2014 | Zhang et al. |
| 8,734,511 B2 | 5/2014 | Weeber et al. |
| 8,771,348 B2 | 7/2014 | Zhao |
| 8,992,611 B2 | 3/2015 | Zhao et al. |
| 9,069,185 B2 | 6/2015 | Zhao |
| 9,078,745 B2 | 7/2015 | Zhang et al. |
| 9,089,421 B2 | 7/2015 | Carson et al. |
| 9,122,074 B2 | 9/2015 | Piers et al. |
| 9,223,148 B2 | 12/2015 | Fiala et al. |
| 9,304,329 B2 | 4/2016 | Zhao |
| 9,320,594 B2 | 4/2016 | Schwiegerling |
| 9,335,563 B2 | 5/2016 | Weeber |
| 9,335,564 B2 | 5/2016 | Choi et al. |
| 9,474,595 B2 | 10/2016 | Zhao et al. |
| 9,901,441 B2 | 2/2018 | Barrett et al. |
| 10,175,505 B2 | 1/2019 | Muschielok et al. |
| 10,197,815 B2 | 2/2019 | Weeber et al. |
| 10,226,326 B2 | 3/2019 | Zhao |
| 10,278,811 B2 | 5/2019 | Choi et al. |
| 10,420,638 B2 | 9/2019 | Hong et al. |
| 10,426,599 B2 | 10/2019 | Choi et al. |
| 10,531,950 B2 | 1/2020 | Tiwari et al. |
| 10,588,738 B2 | 3/2020 | Rosen et al. |
| 10,698,234 B2 | 6/2020 | Zhao |
| 10,831,040 B2 | 11/2020 | Dobschal et al. |
| 10,945,834 B2 | 3/2021 | Bor et al. |
| 11,000,361 B2 | 5/2021 | Hong et al. |
| 11,022,815 B2 | 6/2021 | Weeber |
| 2006/0238702 A1 | 10/2006 | Glick et al. |
| 2007/0282438 A1 | 12/2007 | Hong et al. |
| 2008/0147185 A1 | 6/2008 | Hong et al. |
| 2009/0088840 A1* | 4/2009 | Simpson ............ G02C 7/044 623/6.11 |
| 2009/0210054 A1 | 8/2009 | Weeber et al. |
| 2010/0131060 A1* | 5/2010 | Simpson ............ G02C 7/041 623/6.24 |
| 2010/0312336 A1 | 12/2010 | Hong et al. |
| 2011/0149236 A1 | 6/2011 | Weeber |
| 2012/0140166 A1* | 6/2012 | Zhao ............... G02C 7/041 351/159.44 |
| 2014/0005781 A1* | 1/2014 | Zhao ............... A61F 2/1613 623/6.17 |
| 2014/0303725 A1* | 10/2014 | Barrett ............. A61F 2/1613 623/6.23 |
| 2016/0262876 A1 | 9/2016 | DeBoer et al. |
| 2017/0239038 A1* | 8/2017 | Choi ............... G02C 7/041 |
| 2017/0252151 A1 | 9/2017 | Mackool |
| 2018/0092739 A1 | 4/2018 | Pagnoulle et al. |
| 2018/0147052 A1 | 5/2018 | Hong et al. |
| 2018/0333255 A1 | 11/2018 | Weeber et al. |
| 2018/0373060 A1 | 12/2018 | Knox et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |
| 2019/0314148 A1 | 10/2019 | Liu |
| 2019/0365528 A1 | 12/2019 | Choi et al. |
| 2020/0038172 A1 | 2/2020 | Hussain et al. |
| 2020/0085569 A1 | 3/2020 | Kaschke et al. |
| 2021/0030532 A1 | 2/2021 | Hong et al. |
| 2021/0196451 A1 | 7/2021 | Rosen et al. |
| 2021/0196452 A1 | 7/2021 | Gounou et al. |
| 2021/0196453 A1 | 7/2021 | Rosen et al. |
| 2021/0220118 A1 | 7/2021 | Choi et al. |

FOREIGN PATENT DOCUMENTS

| | | |
|---|---|---|
| JP | 2016150213 A | 8/2016 |
| JP | 6504332 B1 | 4/2019 |
| WO | 0241806 A1 | 5/2002 |
| WO | 2006067255 A1 | 6/2006 |
| WO | 2012028755 A1 | 3/2012 |
| WO | 2019130030 A1 | 7/2019 |
| WO | 2020132703 A1 | 6/2020 |

OTHER PUBLICATIONS

Castignoles F., et al., "Comparison of the Efficiency, MTF and Chromatic Properties of Four Diffractive Bifocal Intraocular Lens Designs," Optics Express, Mar. 2010, vol. 18 (5), pp. 5245-5256.

Cohen A.L., "Practical Design of a Bifocal Hologram Contact Lens or Intraocular Lens," Applied Optics, Jul. 1, 1992, vol. 31 (19), pp. 3750-3754.

Morlock, R., et al., "Patient-Reported Spectacle Independence Questionnaire (PRSIQ): Development and Validation, "American Journal of Ophthalmology, Jun. 2017, vol. 178, pp. 101-114.

Sokolowski M., et al. "Hybrid Heptafocal Intraocular Lenses," Optica Applicata, Dec. 2015, vol. 45 (3), pp. 285-298.

* cited by examiner

FIG. 8
Through Frequency MTF

FIG. 9
Cross section Far Focus PSF

ACHROMATIC LENSES FOR VISION TREATMENT

CROSS REFERENCE TO RELATED APPLICATIONS

This application claims priority to U.S. Provisional Patent Application No. 62/955,341, filed on Dec. 30, 2019, the entire contents of which are hereby incorporated by reference.

BACKGROUND

Embodiments of the present disclosure relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL."

Monofocal IOLs are intended to provide vision correction at one distance only, usually the far focus. At the very least, since a monofocal IOL provides vision treatment at only one distance and since the typical correction is for far distance, spectacles are usually needed for good vision at near distances and sometimes for good vision at intermediate distances. The term "near vision" generally corresponds to vision provided when objects are at a distance from the subject eye at equal; or less than 1.5 feet. The term "distant vision" generally corresponds to vision provided when objects are at a distance of at least ab out 5-6 feet or greater. The term "intermediate vision" corresponds to vision provided when objects are at a distance of about 1.5 feet to about 5-6 feet from the subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

There have been various attempts to address limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near (add) power of about 3.0 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may also be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. While multifocal ophthalmic lenses typically provide adequate near and far vision, intermediate vision may be compromised.

Improvements may also be found in the field of achromats. Achromatic lenses may be utilized to improve color contrast of a lens, however, if such achromats are provided as diffractive patterns then undesired visual effects may result, such as glare or halos. Improvements in lenses having achromats are thus desired.

BRIEF SUMMARY

Embodiments herein described include ophthalmic lenses including an optic having a central region disposed about an optical axis and a peripheral region extending outward from the central region, with a diffractive achromat positioned on the peripheral region, and the central region lacking an achromat, and a base power for distance of the central region being the same as a base power for distance of the peripheral region.

The optic may include a transition between the central region and the peripheral region at which a base curvature of the optic changes. The central region may be adjacent to the peripheral region. The base power for distance of the peripheral region may have a distance power of the diffractive achromat combined with a distance refractive power of the peripheral region. The optic may also extends outward from the optical axis to an outer periphery of the optic, and a base power for distance of the optic may be the same from the optical axis to the outer periphery of the optic.

The central region may be a refractive region, and the base power for distance of the central region may be a refractive power. The central region may extend outward from the optical axis to a radius of at least 1 millimeter, of at least 1.5 millimeters, or of at least 2 millimeters. The central region in other embodiments may comprise an extended depth of focus diffractive region, or utilize bifocality, trifocality, or aperiodic designs (or may be a refractive extended depth of focus region).

Embodiments herein described include a method including fabricating an optic for an ophthalmic lens, the optic having a central region disposed about an optical axis and a peripheral region extending outward from the central region, with a diffractive achromat positioned on the peripheral region, and the central region lacking an achromat, and a base power for distance of the central region being the same as a base power for distance of the peripheral region.

The method may include receiving an ophthalmic lens prescription, and fabricating the optic based on the ophthalmic lens prescription. The method may include determining a profile of one or more of the central region or the diffractive achromat based on the ophthalmic lens prescription. The base power for distance of the peripheral region may comprise a distance power of the diffractive achromat combined with a distance refractive power of the peripheral region. This method of fabrication may be used to fabricate any lens disclosed herein.

Embodiments herein described include a system for fabricating an ophthalmic lens. The system may include a processor configured to determine at least a portion of a profile of an optic having a central region disposed about an optical axis and a peripheral region extending outward from the central region, with a diffractive achromat positioned on the peripheral region, and the central region lacking an achromat, and a base power for distance of the central region being the same as a base power for distance of the peripheral region. The system may include a manufacturing assembly that fabricates the optic based on the profile.

The system may further include an input for receiving an ophthalmic lens prescription, and the processor may be configured to determine a profile of one or more of the central region or the diffractive achromat based on the ophthalmic lens prescription. The base power for distance of the peripheral region may comprise a distance power of the diffractive achromat combined with a distance refractive power of the peripheral region. The optic extends outward from the optical axis to an outer periphery of the optic, and a base power for distance of the optic is the same from the optical axis to the outer periphery of the optic. This system for fabricating may be used to fabricate any lens disclosed herein.

DETAILED DESCRIPTION

FIGS. 1A, 1B, 2A, 2B, 3A and 3B illustrate multifocal IOL lens geometries, aspects of which are described in U.S. Patent Publication No. 2011-0149236 A1, which is hereby incorporated by reference in its entirety.

Figure 1A:
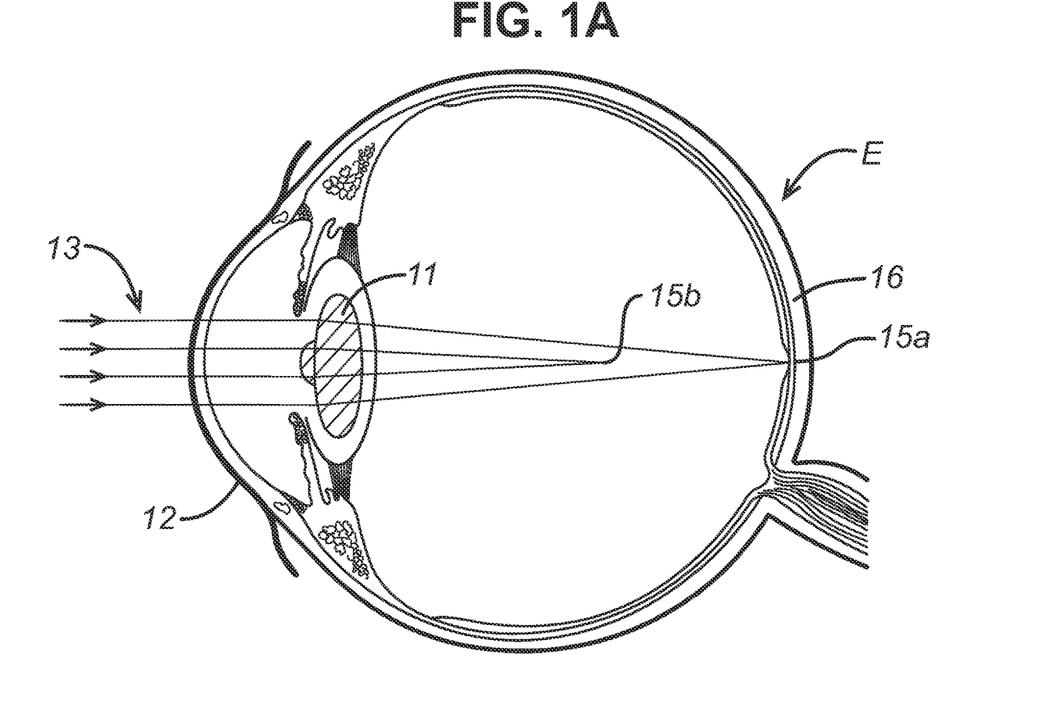
FIG. 1A illustrates a cross-sectional view of an eye with an implanted multifocal refractive intraocular lens.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens. One or more support elements may be configured to secure the lens 11 to a patient's eye.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
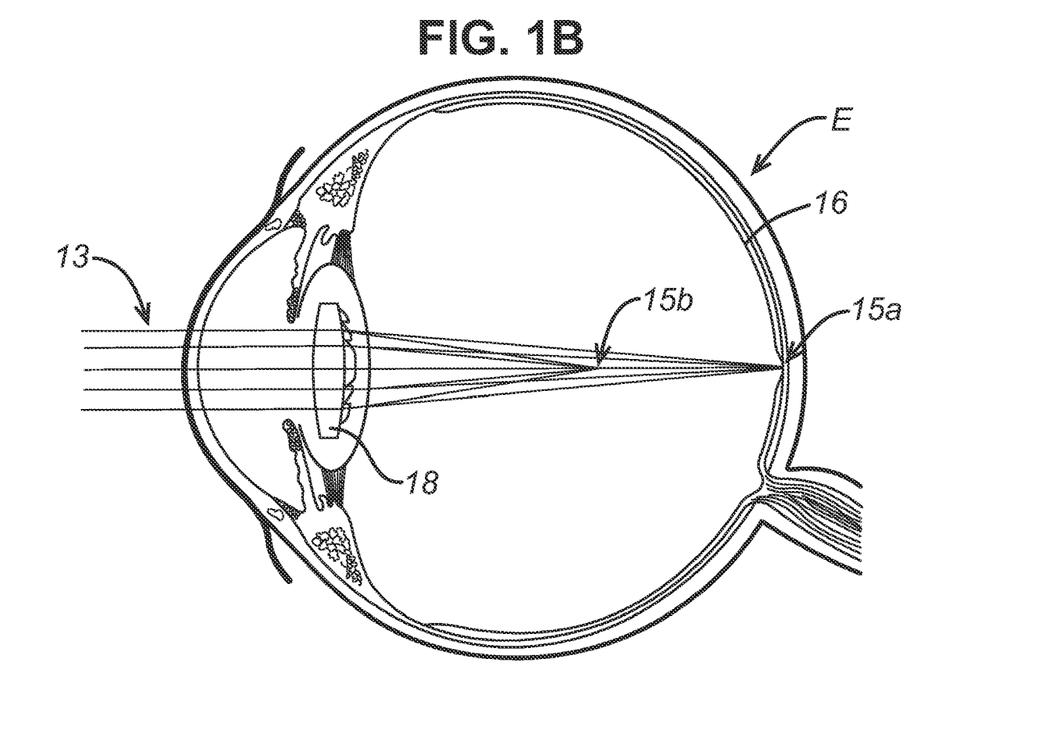
FIG. 1B illustrates a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative power, and that diffractive power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15a on retina 16 for viewing distant objects and a near field focus 15b for viewing objects close to the eye. Depending on the distance from the source of light 13, the focus on retina 16 may be the near field focus 15b instead. Typically, far field focus 15a is associated with $0^{th}$ diffractive order and near field focus 15b is associated with the $1^{st}$ diffractive order, although other orders may be used as well.

Bifocal ophthalmic lens 18 typically distributes the majority of light energy into two viewing orders, often with the goal of splitting imaging light energy about evenly (50%: 50%), one viewing order corresponding to far vision and one viewing order corresponding to near vision, although typically, some fraction goes to non-viewing orders.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, pseudophakic IOLs, other forms of intraocular implants, spectacles, and even laser vision correction.

Figure 2A:
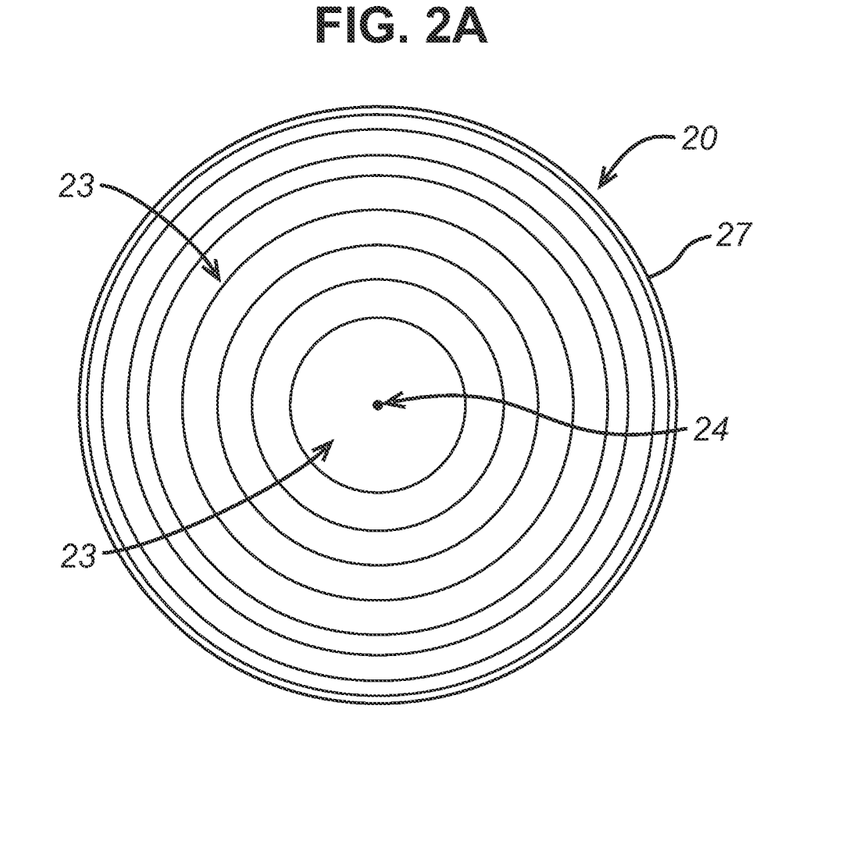
FIG. 2A illustrates a front view of a diffractive multifocal intraocular lens.
Figure 2B:
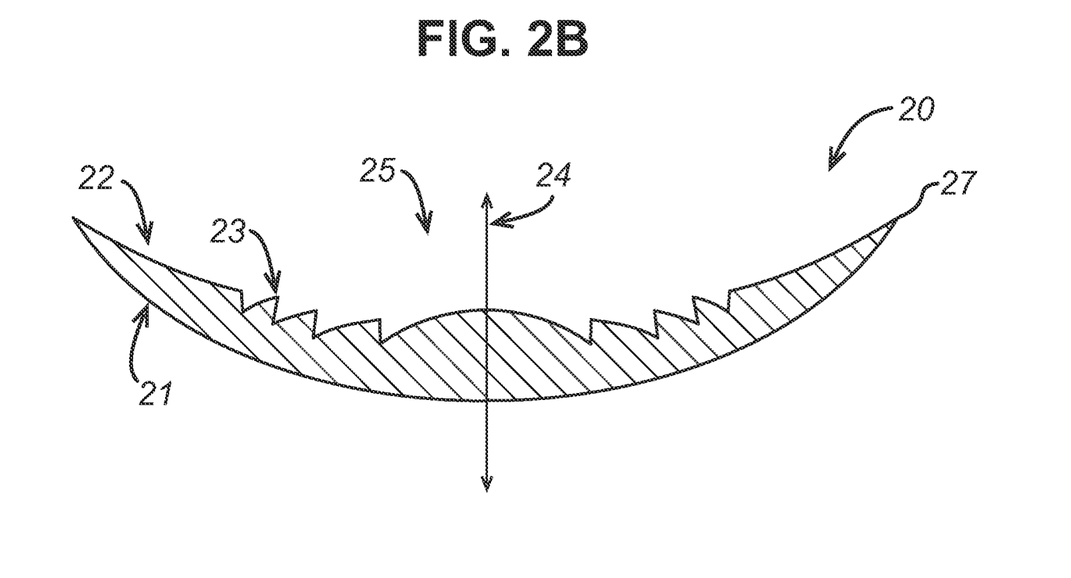
FIG. 2B illustrates a cross-sectional view of a diffractive multifocal intraocular lens.

FIGS. 2A and 2B show aspects of a conventional diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about an optical axis 24. The faces 21, 22, or optical surfaces, extend radially outward from the optical axis 24 to an outer periphery 27 of the optic. The faces 21, 22, or optical surfaces, face opposite each other.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular diffractive zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
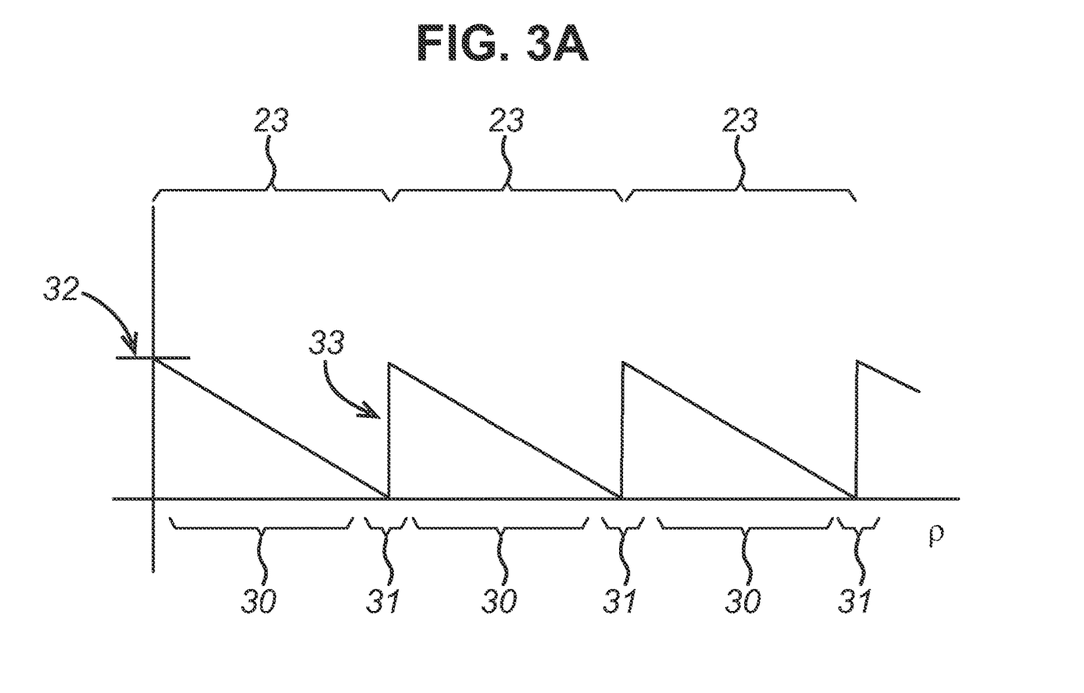
FIGS. 3A-3B are graphical representations of a portion of the diffractive profile of a conventional diffractive multifocal lens.
Figure 3B:
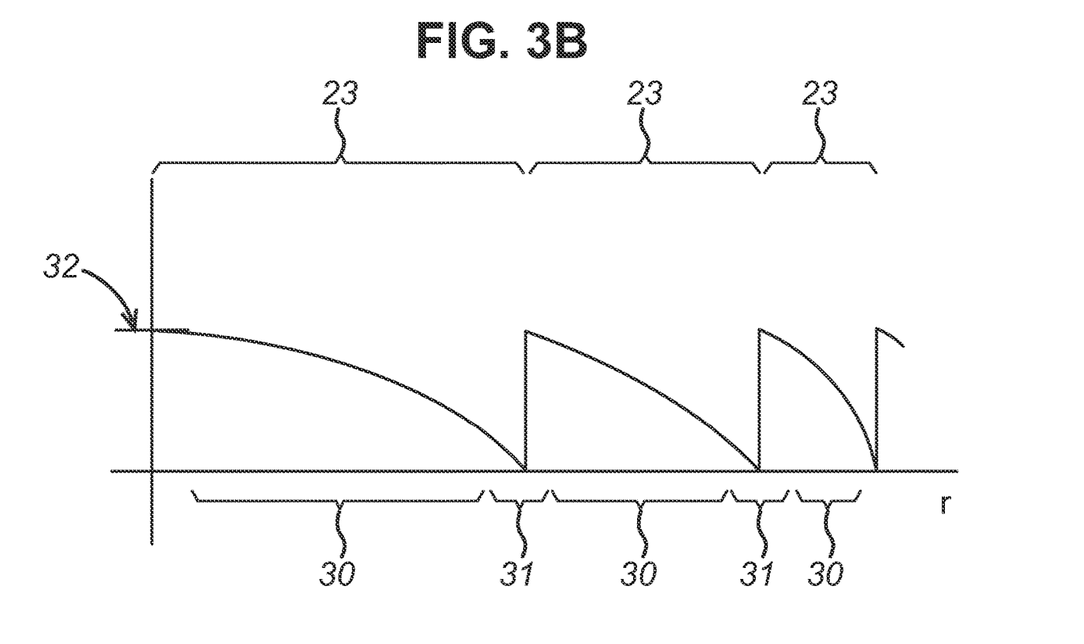

FIGS. 3A and 3B are graphical representations of a portion of a typical diffractive profile of a multifocal lens. While the graph shows only 3 echelettes, typical diffractive lenses extend to at least 9 echelettes to over 32 echelettes. In FIG. 3A, the height 32 of the surface relief profile (from a plane perpendicular to the light rays) of each point on the echelette surface is plotted against the square of the radial distance ($r^2$ or $\rho$) from the optical axis of the lens (referred to as r-squared space). In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 typically has a shape or downward slope that is parabolic as shown in FIG. 3B. The slope of each echelette in r-squared space (shown in FIG. 3A), however, is the same. As for the typical diffractive multifocal lens, as shown here, all echelettes have the same surface area. The area of echelettes 23 determines the diffractive power of lens 20, and, as area and radii are correlated, the diffractive power is also related to the radii of the echelettes. The physical offset of the trailing edge of each echelette to the leading edge of the adjacent echelette is the step height. An exemplary step height between adjacent echelettes is marked as reference number 33 in FIG. 3A. The step heights remain the same in r-squared space (FIG. 3A) and in linear space (FIG. 3B). The step offset is the height offset of the transition zone from the underlying base curve.

Figure 4:
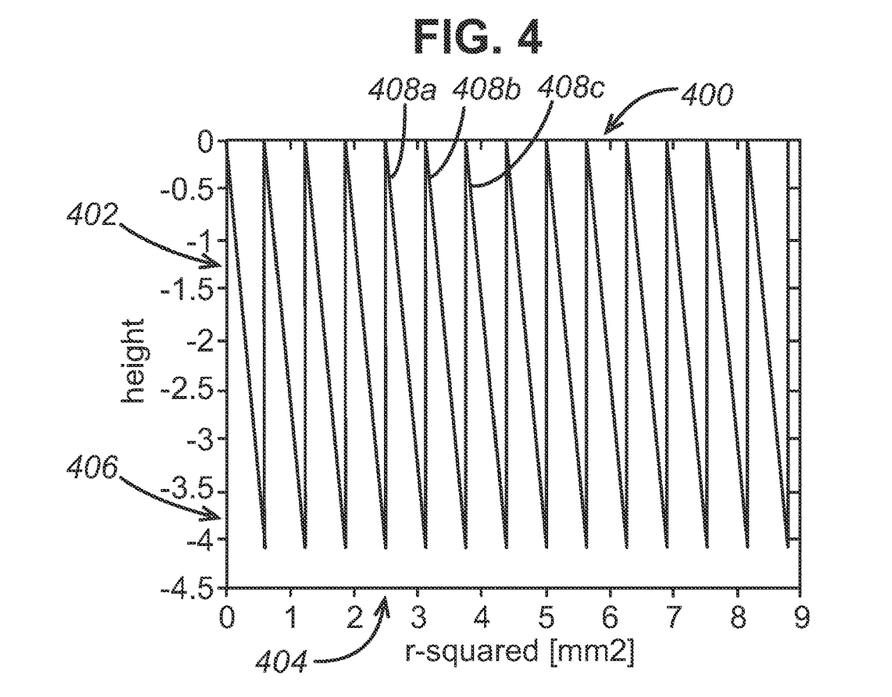
FIG. 4 illustrates a diffractive profile of a diffractive achromat.

Diffractive profiles may be utilized to provide multifocality of lenses and may be utilized to correct chromatic aberrations. A diffractive achromat, including a diffractive profile, may be utilized with an optic to reduce chromatic aberrations. FIG. 4, for example, illustrates a diffractive profile of a diffractive achromat. The diffractive profile 400 of the diffractive achromat is shown relative to the Y axis 402, which represents the phase shift of the diffractive profile 400. The height is shown in units of millimeters (mm), and may represent the distance from the base spherical wavefront generated by the lens. In other embodiments, other units or scalings may be utilized. The height or phase shift of the diffractive profile 400 is shown in relation to the radius on the X axis 404 from the optical axis 406 in r-squared space. The radial coordinate represents the distance from the optical axis 406 in r-squared space, and is shown in units of millimeters squared, although in other embodiments, other units or scalings may be utilized.

The diffractive profile 400 of the diffractive achromat includes a repeating pattern of echelettes (representative echelettes 408a, 408b, 408c are marked) that each have the same width in r-squared space. The step height of each echelette is also the same in the diffractive profile 400. Notably, the diffractive profile 400 of the diffractive achromat extends along the entirety of the optic, extending outward from the optical axis 406 towards the outer periphery of the optic. The entire optic may have the same base curvature, which may be reduced for the entirety of the optic to compensate for the additional optical power of the diffractive achromat.

Figure 5:
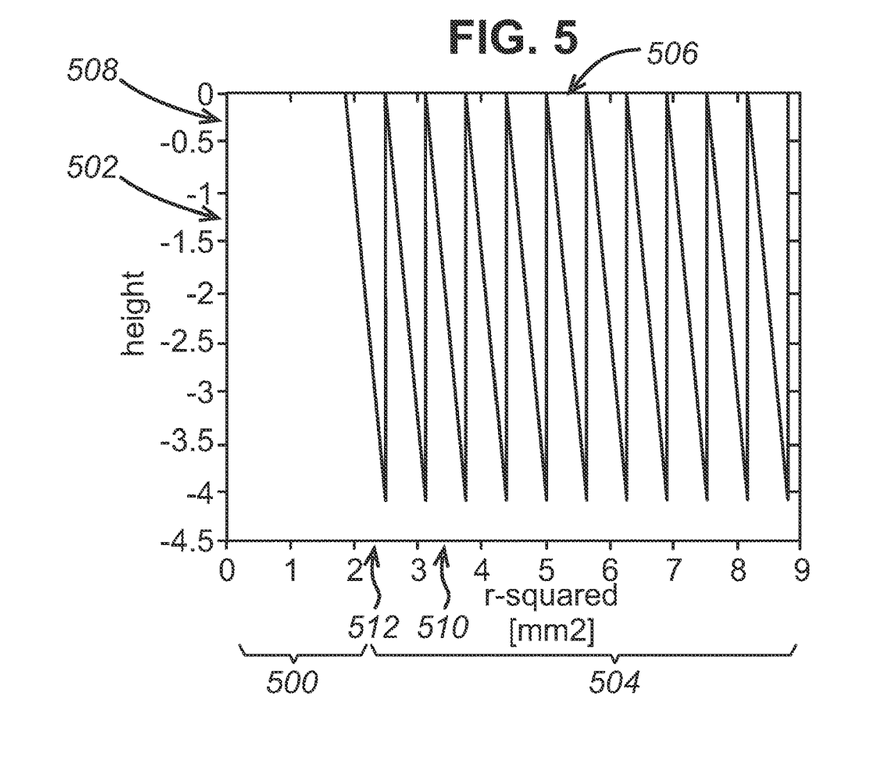
FIG. 5 illustrates an embodiment of an optic including a central region disposed about an optical axis and having a peripheral region extending outward from the central region.

FIG. 5 illustrates an embodiment of an optic including a central region 500 disposed about an optical axis 502 and having a peripheral region 504 extending outward from the central region 500. The central region 500 may lack an achromat. A diffractive achromat having a diffractive profile 506 may be positioned on the peripheral region 504 and may extend outward from the central region 500. The base power for distance of the central region 500 may be the same as a base power for distance of the peripheral region 504. In regard to the diffractive profile 506, the diffractive profile 506 is shown relative to the Y axis 508, which represents the phase shift of the diffractive profile 506. The height is shown in units of millimeters (mm), and may represent the distance from the base spherical wavefront generated by the lens. In other embodiments, other units or scalings may be utilized. The height or phase shift of the diffractive profile 506 is shown in relation to the radius on the X axis 510 from the optical axis 502 in r-squared space. The radial coordinate represents the distance from the optical axis 502 in r-squared space, and is shown in units of millimeters squared, although in other embodiments, other units or scalings may be utilized.

The diffractive profile 506 of the diffractive achromat may be configured similarly as the diffractive profile 400 shown in FIG. 4, and may comprise a plurality of echelettes. The echelettes may repeat on the peripheral region 504 and may have the same width in r-squared space and step height, although in other embodiments other configurations may be utilized. The diffractive profile 506 of the diffractive achromat may extend outward from a transition 512 with the central region 500 to the outer periphery of the optic. In other embodiments, the diffractive profile of the diffractive achromat may extend for another radial distance as desired.

The central region 500 may include the portion of the optic that the optical axis 502 extends through and may extend outward from the optical axis 502 to a desired radial distance. In certain embodiments, the distance may be to about 1.4 millimeters or to a greater or lesser radius as desired (e.g., 1 millimeter, 1.25 millimeters, 1.5 millimeters, 1.75 millimeters, 2 millimeters, among others). The distance may be at least 1 millimeter, at least 1.5 millimeters, or at least 2 millimeters, among other lesser or greater distances. The central region 500 may be adjacent to the peripheral region 504. An achromat, diffractive achromat, or other diffractive profile is not positioned on the central region 500. The central region may be configured to correct ocular aberrations of the patient's eye, including spherical optical aberrations among others. The diffractive achromat positioned on the peripheral region 504 may be configured to correct longitudinal chromatic aberrations.

The base curvature of the optic may be configured such that the base curvature of the central region 500 is greater than the base curvature of the peripheral region 504. The base curvature of the optic is reduced in a direction outward from the optical axis 502 at the transition 512. The base curvature of the central region 500 may be greater than the base curvature of the peripheral region 504 such that the optic has the same base power for distance across the central region 500 and the peripheral region 504 including the diffractive profile 506 of the diffractive achromat. The base power for distance of the peripheral region 504 may comprise a distance power of the diffractive achromat combined with a distance refractive power of the peripheral region 504. The base power for distance of the optic may be the same from the optical axis 502 to the outer periphery of the optic.

The presence of the central region 500 may account for the dilation and contraction of the patient's pupil to provide desired optical effects. When the pupil is contracted and small, the radius of the central region 500 may be set such that light only passes through the central region 500, to reduce the possibility of glare or other adverse optical effects that may be caused by the diffractive achromat. However, when the pupil is dilated and large, light may be provided upon the diffractive achromat, to allow for greater color contrast (which may be at night when the need for color contrast is highest).

The central region 500 may be a refractive region. The base power for distance of the central region 500 may be a refractive power. The central region 500 in other embodiments may comprise an extended depth of focus diffractive region or utilize bifocality, trifocality, aperiodic designs (or may be a refractive extended depth of focus region). Extended depth of focus or multifocality features (which may include a diffractive profile) may be applied to the central region 500 or to the entire optic as desired.

Figure 6:
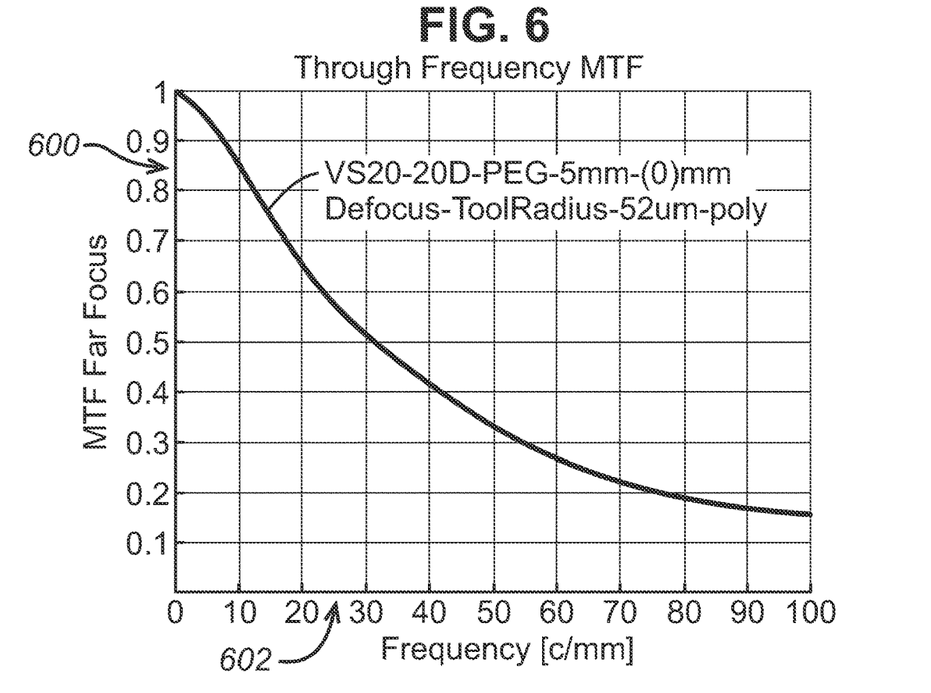
FIG. 6 illustrates a chart of through frequency modulation transfer function (MTF) for an optic that does not include an achromat.
Figure 7:
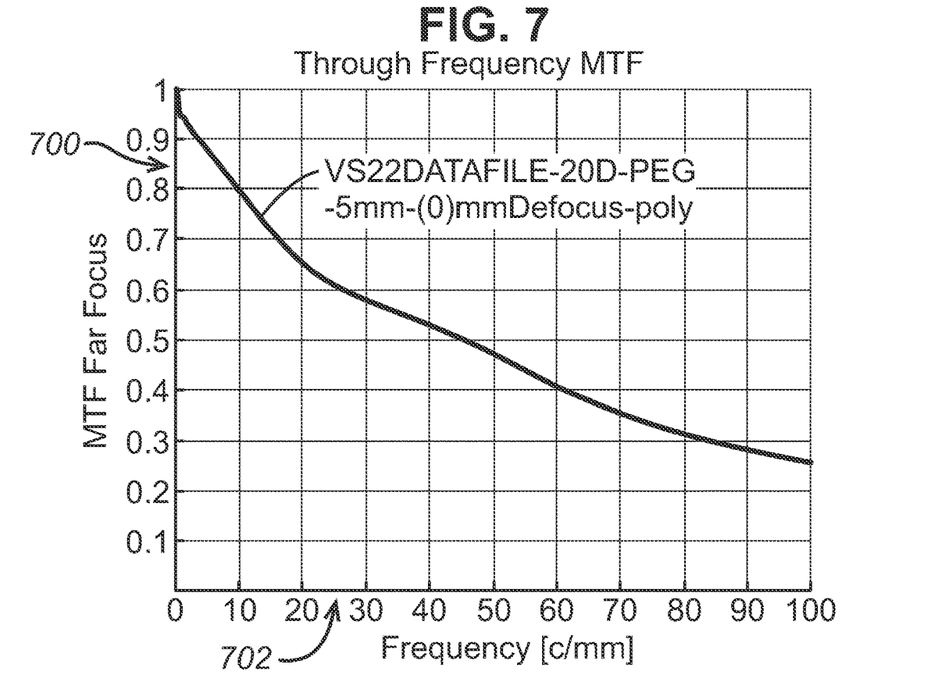
FIG. 7 illustrates a chart of through frequency MTF for an optic that includes an achromat along the entire optical surface.

FIG. 6 illustrates a chart of through frequency modulation transfer function (MTF) for an optic that does not include an achromat. MTF is shown on the Y axis 600, and frequency is shown on the X axis 602. FIG. 7 illustrates a chart of through frequency MTF for an optic that includes an achromat along the entire optical surface, similar to an embodiment shown in FIG. 4. MTF is shown on the Y axis 700, and frequency is shown on the X axis 702.

Figure 8:
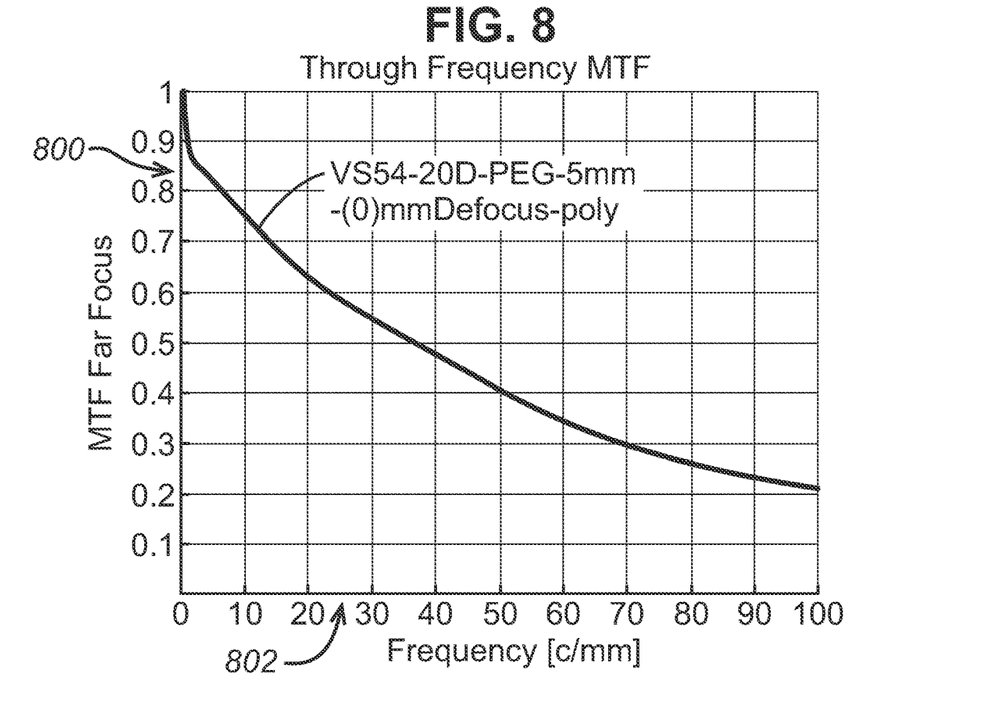
FIG. 8 illustrates a chart of through frequency MTF for an optic that includes a central region and a diffractive achromat on a peripheral region.

FIG. 8 illustrates a chart of through frequency MTF for an optic that includes a central region and a diffractive achromat on a peripheral region, for example as shown in FIG. 5. MTF is shown on the Y axis 800, and frequency is shown on the X axis 802. The MTF for an embodiment as shown in FIG. 5 is shown to preserve most of the contrast gain. However, with reference to FIGS. 9 and 10, which show scatter (point spread function), the embodiment shown in FIG. 5 will have lower incidences of visual symptoms than an embodiment as shown in FIG. 4.

Figure 9:
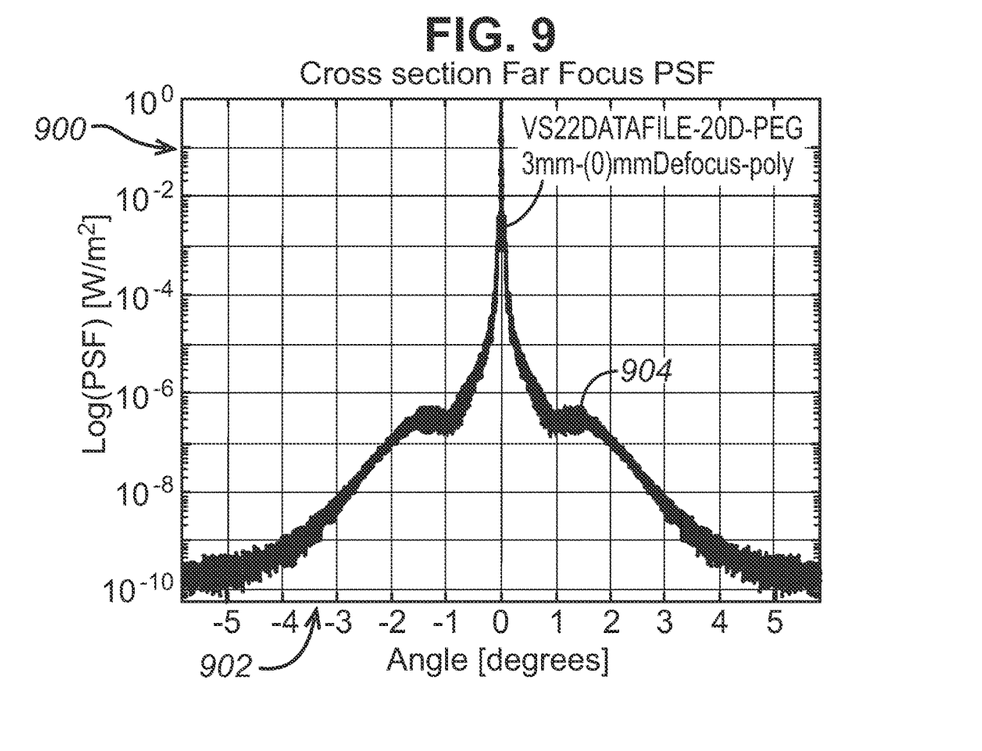
FIG. 9 illustrates a chart of point spread function (PSF) of the optic of FIG. 7.
Figure 10:
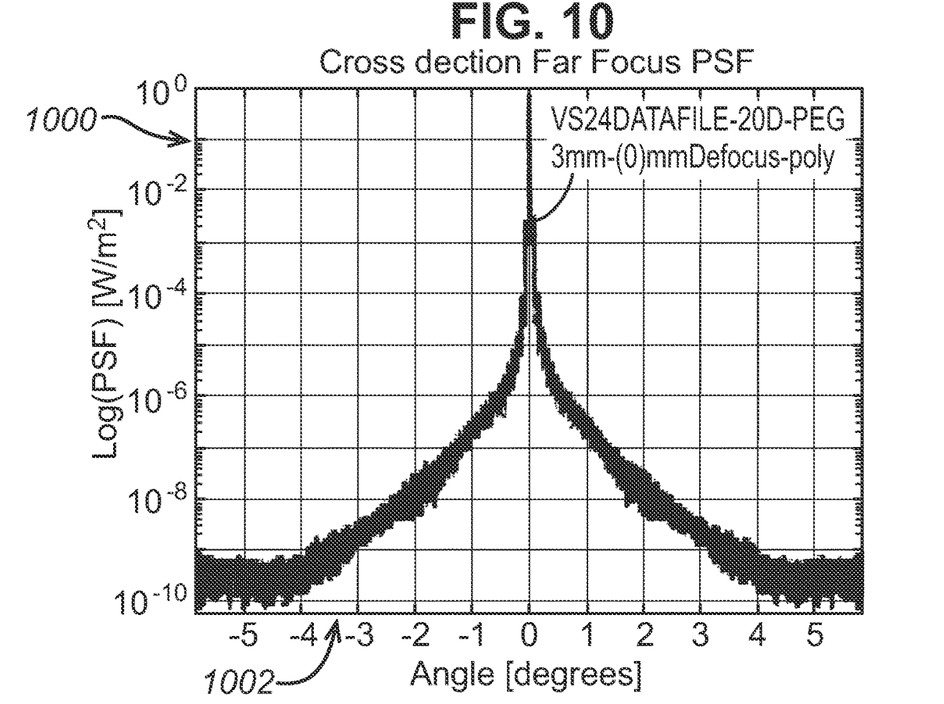
FIG. 10 illustrates a chart of point spread function (PSF) of the optic of FIG. 8.

FIG. 9 illustrates point spread function (PSF) with PSF shown on the Y axis 900 and angle shown on the X axis 902. The PSF is of an embodiment as shown in FIG. 7. The cliff 904 in the profile represents a risk of visual symptoms. FIG. 10 illustrates point spread function (PSF) with PSF shown on the Y axis 1000 and angle shown on the X axis 1002 for an embodiment as shown in FIG. 8. The presence of the cliff is reduced, representing lower risk of visual symptoms for the embodiment shown in FIG. 8 than the embodiment shown in FIG. 7.

An optic for an ophthalmic lens that includes a profile (both the profile of the central region and/or the profile of the diffractive achromat) disclosed herein may be fabricated utilizing a variety of methods. A method may include determining optical aberrations of a patient's eye. Measurements of a patient's eye may be made in a clinical setting, such as by an optometrist, ophthalmologist, or other medical or optical professional. The measurements may be made via manifest refraction, autorefraction, tomography, or a combination of these methods or other measurement methods. The optical aberrations of the patient's eye may be determined. Physical characteristics of the patient's eye may also be measured, such as pupil size and dilated and contracted sizes of the pupil may also be determined.

The measurements of the patient's eye may be placed in an ophthalmic lens prescription, which includes features of an optic that are intended to address the optical aberrations of the patient's eye, as well as features that address the pupillary size (including dilated and contracted sizes) of the patient.

The ophthalmic lens prescription may be utilized to fabricate an optic for the ophthalmic lens. A refractive profile of the central region of the optic may be determined based on the ophthalmic lens prescription, to correct for the optical aberrations of the patient's eye. Such a refractive profile may be applied to the optic. The desired diffractive profile of the diffractive achromat may also be determined. The power of the diffractive achromat may be determined, and the base curvature of the peripheral region having the diffractive achromat may be reduced such that the optic has the same base power for distance in the central region and the peripheral region. The pupillary size of the patient may be utilized to determine a size (radius) of the central region from the optical axis.

The determination of a profile of one or more of the central region or the diffractive achromat and the fabrication of the optic may be performed remotely from the optometrist, ophthalmologist, or other medical or optical professional that performed the measurements of a patient's eye, or may be performed in the same clinical facility of such an individual. If performed remotely, the fabricated optic may be delivered to an optometrist, ophthalmologist, or other medical or optical professional, for being provided to a patient. For an intraocular lens, the fabricated optic may be provided for implant into a patient's eye.

The fabricated optic may be a custom optic fabricated specifically for the patient's eye, or may be fabricated in a manufacturing assembly and then selected by an optometrist, ophthalmologist, or other medical or optical professional for supply to a patient, which may include implantation in the patient's eye.

Figure 11:
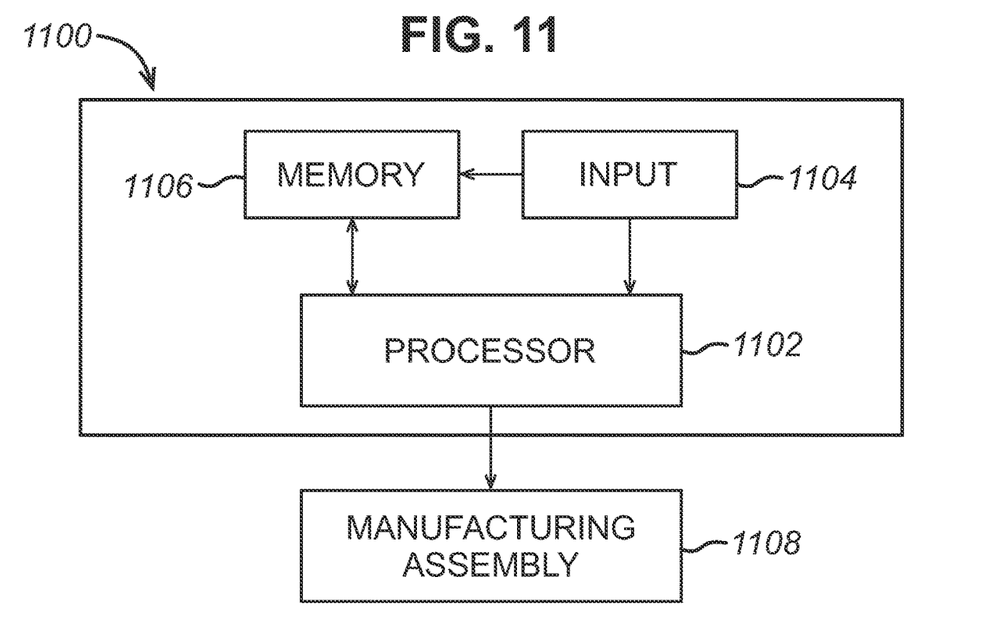
FIG. 11 illustrates an embodiment of a system.

FIG. 11 illustrates an embodiment of a system 1100 that may be utilized to perform all or a portion of the methods disclosed herein. The system 1100 may include a processor 1102, an input 1104, and a memory 1106. In certain embodiments the system 1100 may include a manufacturing assembly 1108.

The processor 1102 may comprise a central processing unit (CPU) or other form of processor. In certain embodiments the processor 1102 may comprise one or more processors. The processor 1102 may include one or more processors that are distributed in certain embodiments, for example, the processor 1102 may be positioned remote from other components of the system 1100 or may be utilized in a cloud computing environment. The memory 1106 may comprise a memory that is readable by the processor 1102. The memory 1106 may store instructions, or features of intraocular lenses, or other parameters that may be utilized by the processor 1102 to perform the methods disclosed herein. The memory 1106 may comprise a hard disk, read-only memory (ROM), random access memory (RAM) or other form of non-transient medium for storing data. The input 1104 may comprise a port, terminal, physical input device, or other form of input. The port or terminal may comprise a physical port or terminal or an electronic port or terminal. The port may comprise a wired or wireless communication device in certain embodiments. The physical input device may comprise a keyboard, touchscreen, keypad, pointer device, or other form of physical input device. The input 1104 may be configured to provide an input to the processor 1102.

The system 1100 may be utilized to perform the methods disclosed herein, such as the processes of determining a profile of one or more of the central region or the diffractive achromat.

The processor 1102 may provide the profile of one or more of the central region or the diffractive achromat to the manufacturing assembly 1108, which may be configured to fabricate the optic for the ophthalmic lens based on the profile of one or more of the central region or the diffractive achromat. The manufacturing assembly 1108 may comprise one or more apparatuses for forming the optic, and may comprise a high volume manufacturing assembly or a low volume manufacturing assembly. The manufacturing assembly 1108 may be used for manufacture remote to a clinic in which measurements of the individual's eye or made, or local to such a clinic. The manufacturing assembly may include apparatuses such as lathe tools, or other lens formation devices to fabricate the optic.

In one embodiment, the processor 1102 may be provided with an ophthalmic lens prescription for the individual's eye that may be provided as discussed herein. The processor 1102 may receive the ophthalmic lens via the input 1104. The system 1100 may fabricate the optic for the ophthalmic lens based on the prescription.

The system 1100 may be configured to fabricate any of the embodiments of ophthalmic lenses disclosed herein.

In one embodiment, a profile as shown in FIG. 5 may be positioned on a surface of a lens that is opposite an aspheric surface. The aspheric surface on the opposite side of the lens may be designed to reduce corneal spherical aberration of the patient.

In one embodiment, one or both surfaces of the lens may be aspherical, or include a refractive surface designed to extend the depth of focus, or create multifocality.

Any of the embodiments of lens profiles discussed herein may be apodized to produce a desired result. The apodization may result in the step heights and step offsets of the echelettes being gradually varied according to the apodization, as to gradually increasing the amount of light in the distance focus as a function of pupil diameter.

The features of the optics disclosed herein may be utilized by themselves, or in combination with refractive profiles of the optics and/or with other features providing for correction of chromatic aberrations.

The ophthalmic lenses disclosed herein in the form of intraocular lenses are not limited to lenses for placement in the individual's capsular bag. For example, the intraocular lenses may comprise those positioned within the anterior chamber of the eye. In certain embodiments the intraocular lenses may comprise "piggy back" lenses or other forms of supplemental intraocular lenses.

Features of embodiments may be modified, substituted, excluded, or combined as desired.

In addition, the methods herein are not limited to the methods specifically described, and may include methods of utilizing the systems and apparatuses disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An ophthalmic lens comprising:
    an optic having a central region disposed about an optical axis and a peripheral region extending outward from the central region, wherein a diffractive achromat is positioned on the peripheral region and is configured to correct longitudinal chromatic aberrations and includes a plurality of echelettes each having a same width in r-squared space, and the central region lacks an achromat, and wherein a base power for distance of the central region is the same as a base power for distance of the peripheral region, and
    wherein a portion of the peripheral region that the diffractive achromat is positioned on has a base curvature that is different than a base curvature of the central region.

2. The ophthalmic lens of claim 1, wherein the optic includes a transition between the central region and the portion of the peripheral region that the diffractive achromat is positioned on at which a base curvature of the optic changes from the base curvature of the central region to the base curvature of the portion of the peripheral region that the diffractive achromat is positioned on.

3. The ophthalmic lens of claim 2, wherein the base curvature of the optic is reduced in a direction outward from the optical axis at the transition.

4. The ophthalmic lens of claim 1, wherein the central region is adjacent to the peripheral region.

5. The ophthalmic lens of claim 1, wherein the base power for distance of the peripheral region comprises a distance power of the diffractive achromat combined with a distance refractive power of the peripheral region.

6. The ophthalmic lens of claim 1, wherein the optic extends outward from the optical axis to an outer periphery of the optic, and a base power for distance of the optic is the same from the optical axis to the outer periphery of the optic.

7. The ophthalmic lens of claim 1, wherein the base power for distance of the central region is a refractive power.

8. The ophthalmic lens of claim 1, wherein the central region is a refractive region.

9. The ophthalmic lens of claim 1, wherein the central region extends outward from the optical axis to a radius of at least 1 millimeter.

10. The ophthalmic lens of claim 1, wherein the central region extends outward from the optical axis to a radius of at least 1.5 millimeters.

11. The ophthalmic lens of claim 1, wherein the central region extends outward from the optical axis to a radius of at least 2 millimeters.

12. The ophthalmic lens of claim 1, wherein the base curvature of the central region is greater than the base curvature of the portion of the peripheral region that the diffractive achromat is positioned on.

13. The ophthalmic lens of claim 1, wherein the base power for distance of the optic is the same from the optical axis to an outer periphery of the optic.

14. The ophthalmic lens of claim 1, wherein the entire optic has the same base power for distance.

15. The ophthalmic lens of claim 1, wherein the diffractive achromat extends to an outer periphery of the optic.

16. The ophthalmic lens of claim 1, wherein the central region is configured to correct spherical optical aberrations.

17. The ophthalmic lens of claim 1, wherein the central region includes an extended depth of focus diffractive region or a multifocality design.

18. The ophthalmic lens of claim 1, wherein the plurality of echelettes each have a same step height.

* * * * *